(12) United States Patent
Kaji et al.

(10) Patent No.: US 7,910,764 B2
(45) Date of Patent: Mar. 22, 2011

(54) POLYMETHYLALUMINOXANE PREPARATION, METHOD OF PRODUCING THE SAME, POLYMERIZATION CATALYST, AND POLYMERIZATION METHOD OF OLEFINS

(75) Inventors: Eiichi Kaji, Yamaguchi (JP); Kouji Toyota, Yamaguchi (JP); Hideki Kanazawa, Yamaguchi (JP)

(73) Assignee: Tosoh Finechem Corporation, Yamaguchi (JP)

( * ) Notice: Subject to any disclaimer, the term of this patent is extended or adjusted under 35 U.S.C. 154(b) by 45 days.

(21) Appl. No.: 10/593,579

(22) PCT Filed: Mar. 18, 2005

(86) PCT No.: PCT/JP2005/004952
§ 371 (c)(1),
(2), (4) Date: Sep. 20, 2006

(87) PCT Pub. No.: WO2005/090363
PCT Pub. Date: Sep. 29, 2005

(65) Prior Publication Data
US 2007/0197745 A1 Aug. 23, 2007

(30) Foreign Application Priority Data
Mar. 22, 2004 (JP) .................. 2004-081911

(51) Int. Cl.
*C07F 5/06* (2006.01)
*B01J 31/14* (2006.01)
*C08F 4/602* (2006.01)

(52) U.S. Cl. ........ 556/179; 556/182; 502/103; 502/152; 526/160; 526/165

(58) Field of Classification Search .................. 556/179, 556/182; 502/103, 152; 526/160, 165
See application file for complete search history.

(56) References Cited

U.S. PATENT DOCUMENTS

| | | | |
|---|---|---|---|
| 5,831,109 A * | 11/1998 | Smith et al. ................... | 556/179 |
| 2003/0195307 A1 | 10/2003 | Kaji et al. | |
| 2004/0242808 A1 | 12/2004 | Mink et al. | |

FOREIGN PATENT DOCUMENTS

| | | |
|---|---|---|
| CN | 1564830 | 1/2005 |
| EP | 0 324 856 | 7/1989 |
| EP | 0 561 476 | 9/1993 |
| EP | 1 352 913 | 10/2003 |
| JP | 2004-182963 | 7/2004 |
| JP | 2005-502741 | 1/2005 |
| KR | 10-2004-0034736 | 4/2004 |
| TW | 588062 | 5/2004 |
| WO | 97/23288 | 7/1997 |
| WO | 03/022890 | 3/2003 |

OTHER PUBLICATIONS

Supplementary European Search Report issued Sep. 22, 2009, in corresponding European Application No. 05 72 1138.
Henri Cramail et al., "New synthetic route to methylaluminoxane for ethylene polymerization in the presence of zirconocene", XP-002545405, C.R. Chimie, May 2002, pp. 49-52.

* cited by examiner

*Primary Examiner* — Caixia Lu
(74) *Attorney, Agent, or Firm* — Wenderoth, Lind & Ponack, L.L.P.

(57) ABSTRACT

A polymethylaluminoxane preparation exhibiting excellent storage stability with a high yield is provided. A polymethylaluminoxane preparation is formed by thermal decomposition of an alkylaluminum compound having an aluminum-oxygen-carbon bond, the alkylaluminum compound being formed by a reaction between trimethylaluminum and an oxygen-containing organic compound. In this preparation, (i) the oxygen-containing organic compound reacting with trimethylaluminum is an aliphatic or aromatic carboxylic acid represented by the general formula (I), $$R^1-(COOH)_n \quad (I),$$

wherein $R^1$ represents a hydrocarbon group of C1-C20 straight or branched alkyl groups, alkenyl groups or aryl groups, and n represents an integer of 1 to 5;

(ii) a mole fraction of methyl groups originating from trimethylaluminum, relative to the total moles of methyl groups existing in the generated polymethylaluminoxane preparation is not more than 26 mol %; and (iii) the generated polymethylaluminoxane preparation has a viscosity of not more than $2.1 \times 10^{-3}$ Pa·sec at 40° C.

5 Claims, 2 Drawing Sheets

FIG.1

○ : Samples in which deposition of gels was observed in 90 days.
□ : Samples in which formation of gels and increase in viscosity were not observed in 90 days.

FIG.2

POLYMETHYLALUMINOXANE PREPARATION, METHOD OF PRODUCING THE SAME, POLYMERIZATION CATALYST, AND POLYMERIZATION METHOD OF OLEFINS

BACKGROUND OF THE INVENTION

1. Field of the Invention

The present invention relates to a polymethylaluminoxane preparation used as a catalyst for polymerization of olefins, and a production method thereof, a polymerization catalyst using the polymethylaluminoxane preparation as a catalytic component, and a polymerization method of olefins.

2. Description of the Related Art

Aluminoxane is a condensation product, generally prepared by a partial hydrolysis of an organic aluminum compound, and known to be useful as a promoter component that efficiently activates a transition metal compound which is a main catalyst. It is widely known that a polymethylaluminoxane preparation prepared by using trimethylaluminum as an organic aluminum compound, a raw material thereof, in particular, exhibits an excellent promoter performance. Examples can be found, for example, in (Patent document 1), (Patent document 2), (Patent document 3), (Patent document 4), (Patent document 5), (Patent document 6), and the like.

Up to know, many proposals have been made regarding production of a polymethylaluminoxane preparation. A first exemplary proposal involves controlling reaction between water and trialkylaluminum using an inorganic salt having water of crystallization such as copper sulfate or aluminum sulfate. Examples of such proposal include (Patent document 7), (Patent document 8), (Patent document 9), and (Patent document 10). In these proposals, it is necessary to grind a solid inorganic salt into adequately fine particles in order to efficiently use the water of crystallization, and long reaction time is required. Furthermore, a large part of the generated polymethylaluminoxane preparation is adsorbed to the inorganic salt, so that the yield is greatly reduced.

A second exemplary proposal for the production method of polymethylaluminoxane preparation involves adding water that is finely dispersed in an inert solvent, to trimethylaluminum dissolved and diluted in an inert solvent. Examples of such proposal include (Patent document 11), (Patent document 12), (Patent document 13), (Patent document 14), and (Patent document 15). In the reaction between water and trimethylaluminum, however, since solid or gel is inevitably formed as one form of trimethylaluminum having excessively hydrolyzed, the reaction yield based on aluminum is decreased. Also found is an attempt to suppress generation of solids or gels by conducting hydrolysis in an extremely low concentration and controlling the degree of hydrolysis of trialkylaluminum relatively to low. However, such preparation method will lead significant decrease in generation efficiency of the polymethylaluminoxane preparation.

T. Mole et al. have reported that a polymethylaluminoxane preparation can be obtained by thermal decomposition of an aluminum alkoxide compound that is generated by a reaction between trimethylaluminum and an oxygen-containing compound such as tertiary alcohols, ketones, and carboxylic acids. Examples of such report include (Non-patent document 1), (Non-patent document 2), and (Non-patent document 3). The methylaluminoxane preparation prepared in this manner is described in (Non-patent document 4) as being unsuited for a promoter of a transition metal complex which is a main catalyst for polymerization of olefins, and hence the above method was not recognized as a useful preparation method of polymethylaluminoxane.

According to a description of (Patent document 7) by G. M. Smith et al., nonhydrolytic conversion of a precursor for polymethylaluminoxane formed by treating trialkylaluminum with an organic compound having a carbon-oxygen bond gives a polymethylaluminoxane preparation essentially containing no trimethylaluminum, and the polymethylaluminoxane preparation thus obtained is catalytically useful. The term "nonhydrolytic conversion" normally means thermal decomposition reaction. It is also described that addition of a Lewis acid such as polymethylaluminoxane preparation promotes the thermal decomposition reaction and reduces the time required for the thermal decomposition. As the reports regarding this concept, (Patent document 16) and (Non-patent document 5) can be recited. (Non-patent document 5) discloses that, as a catalyst for thermal decomposition, polymethylaluminoxane preparation and aluminum chloride have excellent catalytic actions. However, when a nonhydrolytically prepared polymethylaluminoxane preparation is used as a catalytic component for polymerization of olefins, use of a halogen-containing alkyl aluminum such as aluminum chloride is a direct cause of decrease in polymerization activity. The approach of using a polymethylaluminoxane preparation as a catalyst for thermal decomposition imposes one of limitations in practical production of polymethylaluminoxane preparation. One problem lies in that due to trimethylaluminum essentially contained in a polymethylaluminoxane preparation as a raw material, when one determines a quantity ratio between trimethylaluminum and an oxygen-containing compound, some error occurs in the set value depending on the composition and amount of the added polymethylaluminoxane preparation. Therefore, compounds that have been known heretofore as a catalyst for thermal decomposition are not favorable from the view point of industrial production of polymethylaluminoxane preparation.

S. A. Sangokoya et al. report in (Patent document 17) that nonhyrolytic conversion of the above polymethyl aluminoxane precursor is promoted by adding a catalytic amount of water. This proposal solves a part of problem caused by addition of polymethylaluminoxane as a catalyst for thermal decomposition. However, if the added amount of water is excess in the case of adopting the nonhydrolytic preparation method of polymethylaluminoxane, gels are formed to lower the yield.

[Patent document 1] Japanese Patent Laid-Open Publication No. Sho 58-19309

[Patent document 2] Japanese Patent Laid-Open Publication No. Sho 60-35005

[Patent document 3] Japanese Patent Laid-Open Publication No. Sho 62-234009

[Patent document 4] Japanese Patent Laid-Open Publication No. Sho 63-234009

[Patent document 5] Japanese Patent Laid-Open Publication No. Sho 64-66214

[Patent document 6] Japanese Patent Laid-Open Publication No. Hei 1-207355

[Patent document 7] Description of U.S. Pat. No. 4,404,344

[Patent document 8] Description of U.S. Pat. No. 4,544,762

[Patent document 9] Description of U.S. Pat. No. 4,665,208

[Patent document 10] Japanese Patent Laid-Open Publication No. Hei 1-258686

[Patent document 11] Description of U.S. Pat. No. 4,730,071

[Patent document 12] Description of U.S. Pat. No. 4,730, 072
[Patent document 13] Japanese Patent Laid-Open Publication No. Hei 2-219805
[Patent document 14] Description of U.S. Pat. No. 5,103, 031
[Patent document 15] Japanese Patent Laid-Open Publication No. Hei 4-235990
[Patent document 16] Pamphlet of WO 97/23288
[Patent document 17] Description of U.S. Pat. No. 6,013, 820
[Non-patent document 1] Australian Journal of Chemistry 27, 1639 (1974)
[Non-patent document 2] Australian Journal of Chemistry 27, 1655 (1974)
[Non-patent document 3] Australian Journal of Chemistry 27, 1665 (1974)
[Non-patent document 4] Comprehensive Organometallic Chemistry II, 1, 452 (1995)
[Non-patent document 5] Organometallics, 20, 5162 (2001)

SUMMARY OF THE INVENTION

It is an object of the present invention to provide a polymethylaluminoxane preparation exhibiting excellent storage stability with a high yield, and to provide a method of producing a desirable olefinic polymer having excellent quality with high industrial efficiency and low costs using the polymethylaluminoxane preparation and a transition metal compound.

Inventors of the present application diligently made researches for solving the problems of the conventional art, and found that the above object can be achieved by a polymethylaluminoxane preparation that is prepared by thermal decomposition of an alkylaluminum compound having an aluminum-oxygen-carbon bond prepared by a reaction between trimethylaluminum and a specific oxygen-containing organic compound, and finally accomplished the present invention. The present invention relates to the following subject matters.

(1) A polymethylaluminoxane preparation generated by thermal decomposition of an alkylaluminum compound having an aluminum-oxygen-carbon bond, the alkylaluminum compound being generated by a reaction between trimethylaluminum and an oxygen-containing organic compound, wherein (i) the oxygen-containing organic compound reacting with trimethylaluminum is an aliphatic or aromatic carboxylic acid represented by the general formula (I), (I)

(wherein $R^1$ represents a hydrocarbon group of C1-C20 straight or branched alkyl groups, alkenyl groups or aryl groups, and n represents an integer of 1 to 5);

(ii) a mole fraction of methyl groups originating from trimethylaluminum, relative to the total moles of methyl groups existing in the generated polymethylaluminoxane preparation is not more than 26 mol %; and (iii) the generated polymethylaluminoxane preparation has a viscosity of not more than $2.1 \times 10^{-3}$ Pa·sec at 40° C.

(2) The polymethylaluminoxane preparation according to the above item (1), wherein the oxygen-containing organic compound represented by the general formula (I) is benzoic acid.

(3) The polymethylaluminoxane preparation according to the above item (1), wherein the oxygen-containing organic compound represented by the general formula (I) is toluic acid.

(4) A method of producing a polymethylaluminoxane preparation having a mole fraction of methyl groups originating from trimethylaluminum, relative to the total moles of methyl groups of not more than 26 mol % and a viscosity of not more than $2.1 \times 10^{-3}$ Pa·sec at 40° C., the method comprising the steps of:

causing trimethylaluminum to react with an oxygen-containing organic compound represented by the general formula (I), (wherein $R^1$ represents a hydrocarbon group of C1-C20 straight or branched alkyl groups, alkenyl groups or aryl groups, and n represents an integer of 1 to 5) to form an alkylaluminum compound having an aluminum-oxygen-carbon bond; and thermally decomposing the alkylaluminum compound, wherein a ratio between a mole number of trimethylaluminum and a mole number of oxygen in the oxygen-containing compound represented by the general formula (I) is in the range of 1.25 to 1.40:1.

(5) The method of producing a polymethylaluminoxane preparation according to the above item (4), wherein the thermal decomposition is conducted in the absence of a Lewis acid compound in production of the polymethylaluminoxane preparation.

(6) The method of producing a polymethylaluminoxane preparation according to the above item (4) or (5), wherein the oxygen-containing organic compound represented by the general formula (I) is benzoic acid.

(7) The method of producing a polymethylaluminoxane preparation according to the above item (4) or (5), wherein the oxygen-containing organic compound represented by the general formula (I) is toluic acid.

(8) A polymerization catalyst for olefins, comprising as catalytic components:

a transition metal compound represented by the general formula (II), (wherein M represents a transition metal element, and $R^5$, $R^6$, $R^7$, and $R^8$ represent organic groups that form together a cycloalkadienyl backbone, such as an alkyl group, an alkoxy group, an aryloxy group, an alkylsilyl group, an alkylamide group, an alkylimide group, an alkylamino group, an alkylimino group, or a halogen atom), and the polymethylaluminoxane preparation according to any one of the above items (1) to (3).

(9) A method of polymerizing olefins using the polymerization catalyst according to the above item (8).

That is, the present invention relates to a polymethylaluminoxane preparation prepared by thermal decomposition of an alkylaluminum compound having an aluminum-oxygen-carbon bond, the alkylaluminum being prepared by a reaction between trimethylaluminum and a specific oxygen-containing organic compound, wherein the oxygen-containing organic compound is a carboxylic acid, and the prepared polymethylaluminoxane preparation solution has a viscosity of not more than $2.1 \times 10^{-3}$ Pa·sec; a production method thereof; a polymerization catalyst for olefins comprising the polymethylaluminoxane preparation and a transition metal compound; and a polymerization method of olefins.

The polymethylaluminoxane preparation of the present invention is easy to handle because of its low solution viscosity, and can keep stability for a long term without necessity of refrigeration storage. The catalyst for olefin polymerization comprising the combination of the polymethylaluminoxane preparation of the invention and a transition metal compound exhibits high polymerization activity in a stable manner.

DETAILED DESCRIPTION OF THE PREFERRED EMBODIMENTS

The details of the present invention will be described below.

A polymethylaluminoxane preparation of the present invention is a composition containing not only an objective polymethylaluminoxane but also trimethylaluminum which is an unreacted raw material (generally called "polymethylaluminoxane preparation").

It is assumed that polymethylaluminoxane in the present invention is a compound comprising a unit represented by the general formula (III):

$$—[(Me)Al—O]_m— \quad (III)$$

(wherein "m" represents an integer from 1 to 60). Polymethylaluminoxane in the present invention may be of a chain structure or a circular structure insofar as it comprises the above unit.

Many of proposals that have been proposed for obtaining a polymethylaluminoxane preparation are based on hydrolysis. In such a case, recovery of aluminum will greatly decrease unless an aluminum concentration in a reaction liquid is made low and an amount of introduced water relative to a raw material, trimethylaluminum is made small. In addition, since trimethylaluminum does not act as a promoter for a transition metal complex such as metallocene catalyst, it is an important problem to control the amount of trimethylaluminum remaining in the polymethylaluminoxane preparation.

Therefore, in most of the documents concerning production of a polymethylaluminoxane preparation by thermal decomposition of an aluminum compound having an aluminum-oxygen-carbon bond, emphasis was put on the possibility of obtaining the polymethylaluminoxane preparation at a quantitative reaction yield and the controllability of amount of trimethylaluminum in the polymethylaluminoxane preparation.

However, since a polymethylaluminoxane preparation will self-associate and form gels which are insoluble in a solvent during storage, improvement in stability of polymethylaluminoxane is also an important problem just like the content of trimethylaluminum and aluminum recovery. In general, the higher the concentration of the polymethylaluminoxane solution and the smaller the amount of trimethylaluminum in the polymethylaluminoxane preparation, the more likely the gels are formed. This phenomenon also depends on the storage temperature of the polymethylaluminoxane, and it is known than the lower the storage temperature, the longer the storage stability is maintained.

Many descriptions concerning use application of an oxygen-containing compound are found in the conventional arts, however no information can be obtained about what kind of oxygen-containing compound can give a polymethylaluminoxane preparation having excellent storage stability. We assumed that there must be an oxygen-containing compound which is suited for a polymethylaluminoxane preparation having excellent long-term storage stability, and found that specific carboxylic acid compounds among a great number of oxygen-containing compounds can give a polymethylaluminoxane preparation having excellent storage stability.

It is also shown in conventional arts that temperature at the time of thermal decomposition largely influences on the storage stability of a polymethylaluminoxane preparation. It is also described that a polymethylaluminoxane preparation prepared at a low temperature has low solution viscosity, and is expected to have excellent storage stability. However, detailed examination about the relationship between solution viscosity and storage stability is not made in any conventional art.

In the present invention, we found existence of a critical viscosity at which the storage stability specifically changes that is unexpectable from the prior-art documents between solution viscosity and storage stability when a specific oxygen-containing compound is used.

Concretely, we prepared different polymethylaluminoxane preparations using carboxylic acid compounds under various conditions, and closely examined the relationship between solution viscosity and storage stability. From such examination, we found that solutions of polymethylaluminoxane preparations having a viscosity at 40° C. of less than $2.1 \times 10^{-3}$ Pa·sec do not generate gels at room temperature in a period of about 90 days, and hence have excellent storage stability.

If the solution viscosity exceeds $2.1 \times 10^{-3}$ Pa·sec at 40° C., deposition of gels is observed in several days, demonstrating that the storage stability of the polymethylaluminoxane preparation is significantly impaired.

In conventional arts, there is a description that a polymethylaluminoxane preparation of solution state or solid state is useful as a catalyst for thermal decomposition of an alkylaluminum compound having an aluminum-oxygen-carbon bond, however no description about an adverse effect thereof can be found. We also found that by adding a polymethylaluminoxane preparation, the storage stability of the generated polymethylaluminoxane preparation is impaired.

It is generally known that gelling of a polymethylaluminoxane preparation is dramatically accelerated when it is exposed to elevated temperatures of about more than 100° C. Accordingly, in order to obtain a polymethylaluminoxane preparation exhibiting high aluminum recovery and excellent storage stability, thermal decomposition should be completed at such a temperature and in such a period that will not cause formation of gels.

From this point of view, we closely examined for a reaction system capable of completing the reaction in such a condition that will not cause formation of gels and not requiring addition of polymethylaluminoxane for increasing the reaction speed of thermal decomposition, and found that when a carboxylic acid compound is used as an oxygen-containing organic compound, generation of the polymethylaluminoxane proceeds at low temperature and in short time without addition of polymethylaluminoxane, and accomplished the present invention.

The polymethylaluminoxane preparation prepared in this manner exerts high activity as a promoter for olefin polymerization in the case when a homogenous polymerization catalyst is used and in the case where it is used as a solid catalyst supported on a microparticle carrier such as silica together with a transition metal catalyst.

For the polymethylaluminoxane preparation of the present invention, any inert hydrocarbon compound can be used as a solvent. Examples of the inert hydrocarbon compound include saturated hydrocarbon compounds such as n-pentane, n-hexane, n-heptane, n-octane, isooctane, and purified kerosene; cyclic aliphatic hydrocarbon compounds such as cyclopentane, cyclohexane, methylcyclohexane, ethylcyclohexane, and cycloheptane; and aromatic hydrocarbon compounds such as benzene, toluene, ethylbenzene, o-xylene, m-xylene, and p-xylene. Among these compounds, n-hexane, n-heptane, n-octane, cyclohexane, methylcyclohexane, and toluene are preferred.

An alkylaluminum compound having an aluminum-oxygen-carbon bond that gives polymethylaluminoxane through thermal decomposition is prepared by a reaction between trimethylaluminum and an oxygen-containing compound. The oxygen-containing compound used herein is a carboxylic acid compound having a COOH group as represented by the general formula (I). In preparation of polymethylaluminoxane, one or more than one such compound may be used. Concrete examples of the oxygen-containing compound represented by the general formula (I) include formic acid, acetic acid, propionic acid, n-butyric acid, n-valeric acid, n-caproic acid, n-enanthic acid, n-caprylic acid, n-pelargonic acid, n-capric acid, n-lauric acid, n-myristic acid, n-stearic acid, oxalic acid, malonic acid, succinic acid, glutaric acid, adipic acid, pimelic acid, suberic acid, azelaic acid, sebacic acid, benzoic acid, phthalic acid, citric acid, tartaric acid, lactic acid, malic acid, and toluic acid. Among these, acetic acid, propionic acid, benzoic acid, phthalic acid, toluic acid, and malonic acid are preferred.

A molar ratio between trimethylaluminum and oxygen atoms of an oxygen-containing organic compound used for synthesis of a polymethylaluminoxane preparation can be arbitrarily selected depending on the use application of the polymethylaluminoxane or for the purpose of controlling the remaining amount of trimethylaluminum. A molar ratio of trimethylaluminum to oxygen atoms of an oxygen-containing organic compound represented by the general formula (I) can be arbitrarily selected within the range of 0.5 to 3.0:1. It is preferably in the range of 1.0 to 1.7:1, and more preferably in the range of 1.25 to 1.4:1.

If the molar ratio between trimethylaluminum and oxygen atoms of an oxygen-containing organic compound is less than 1.25, viscosity of the polymethylaluminoxane preparation increases to cause significant deterioration of storage stability. Contrarily, if the molar ratio between trimethylaluminum and oxygen atoms of an oxygen-containing organic compound is more than 1.40, storage stability is improved due to low viscosity of the polymethylaluminoxane preparation, however, functionality as a promoter for olefin polymerization is impaired due to significant decrease of olefin polymerization activity.

If a molar fraction of methyl groups originating from trimethylaluminum to the total molar number of methyl groups existing in a polymethylaluminum preparation obtained by thermal decomposition of trimethylaluminum and an oxygen-containing compound is more than 26 mol %, an activity in olefin polymerization using the polymethylaluminoxane preparation is impaired, and hence functionality as a promoter for olefin polymerization is impaired.

Thermal decomposition of an aluminum compound having an aluminum-oxygen-carbon bond which is a precursor of a polymethylaluminoxane preparation may be conducted at any temperature between −10° C. and 200° C. Preferably, the temperature is between 30° C. and 150° C., and more preferably between 40° C. and 80° C.

It is known that the reaction speed of thermal decomposition of an aluminum compound having an aluminum-oxygen-carbon bond which is a precursor of a polymethylaluminoxane preparation is improved by addition of a Lewis acid. In general, polymethylaluminoxane that is prepared in advance is used. We examined about influence of added amount of polymethylaluminoxane as a catalyst of thermal decomposition, and found that the stability of the polymethylaluminoxane generated by thermal decomposition differs depending on the added amount of the polymethylaluminoxane. Then, we compared the case where polymethylaluminoxane that is hydrolytically synthesized by using water as an oxygen source is used as a catalyst for thermal decomposition with the case where polymethylaluminoxane that is prepared by thermal decomposition is used as a catalyst for thermal decomposition, and found that the stability of the polymethylaluminoxane significantly decrease when the polymethylaluminoxane prepared by thermal decomposition is used. The above findings imply that the polymethylaluminoxane catalyst added in preparing polymethylaluminoxane by thermal decomposition adversely affects on the stability of the generated polymethylaluminoxane.

Further, since the polymethylaluminoxane that is conventionally used as a catalyst for thermal decomposition is exactly a composition which contains polymethylaluminoxane represented by the general formula (III) and trimethylaluminum which is an unreacted raw material, it is difficult to accurately determine the quantity ratio between an oxygen-containing compound and trimethylaluminum accurately. This also applies to the case where solid aluminoxane from which solvent is removed is used.

As a Lewis acid compound that is conventionally used as a catalyst for thermal decomposition, compounds such as aluminum chloride can be exemplified, however, halogen containing compounds like aluminum chloride are not favorable in most situations where polymethylaluminoxane is used as a promoter of a polymerization catalyst of olefins because they lead decrease of the activity.

From the above findings, it would be desirable to construct a reaction system not requiring use of any catalyst for thermal decomposition.

Concentration of a polymethylaluminoxane preparation in an inert hydrocarbon solvent can be in the range of 6 to 40% by weight, preferably in the range of 6 to 30% by weight, and more preferably in the range of 20 to 25% by weight.

The polymethylaluminoxane preparation of the present invention does not necessarily need a post treatment after reaction, however, low boiling point compounds such as residual trimethylaluminum existing in the solvent may be distilled off under reduced pressure for the purpose of, for example, adjustment of the aluminum concentration as necessary.

In the polymethylaluminoxane preparation of the present invention, an appropriate amount of organic metal compound such as organic aluminum compound may be added during or after reaction for the purpose of controlling Lewis acidity of the polymethylaluminoxane preparation, or further improving the storage stability or the solvent solubility.

The organic aluminum compound added in an appropriate amount to the polymethylaluminoxane preparation of the preset invention can be represented by the following general formula (IV):

$$R^9_p AlX_{3-p} \quad (IV)$$

(wherein $R^9$ represents a hydrocarbon group such as a C1 to C20 straight or branched alkyl group, an alkenyl group or an aryl group, "X" represents a hydrogen atom, a halogen atom, an alkoxy group, or an aryloxy group, and "p" is in the range of 0<p≦3).

Concrete examples of $R^9$ in the general formula (IV) include alkyl groups such as methyl group, ethyl group, propyl group, n-butyl group, isobutyl group, t-butyl group, amyl group, isoamyl group, n-hexyl group, isohexyl group, n-octyl group, and isooctyl group; and aryl groups such as phenyl group, tolyl group, and pentafluorophenyl group. Concrete examples of "X" include halogen atoms such as fluorine, chlorine, bromine, and iodine; alkoxy groups such as methoxy group and ethoxy group; and aryloxy groups such as phenoxy group.

Concrete examples of the organic aluminum compound include alkylaluminums such as trimethylaluminum, triethylaluminum, tripropylaluminum, tri-n-butylaluminum, tri-isobutylaluminum, tri-n-hexylaluminum, and tri-n-octylaluminum; triarylaluminums such as triphenylaluminum, tritolylaluminum, and tris-pentafluorophenylaluminum; and halogen-containing alkylaluminums such as dimethylaluminum chloride and diethylaluminum chloride. These trialkylaluminums may be used singly or in combination. The most preferred organic aluminum compounds and combinations to be added to the polymethylaluminoxane preparation are trimethylaluminum, triisobutylaluminum, tri-n-hexylaluminum or tri-n-octylaluminum, and combinations thereof.

Examples of the organic metal compound other than the organic aluminum compound that can be added to the polymethylaluminoxane of the present invention in an appropriate amount include boron compounds such as triethylboron and tris-pentafluorophenyl boron; and zinc compounds such as diethyl zinc.

The amount of the organic metal compound added to the polymethylaluminoxane preparation can be defined by metal molar quantity of the added organic metal compound, relative to the molar quantity of the aluminum in the polymethylaluminoxane preparation. In practice, an optimum amount of the organic metal compound is added depending on the solvent used for the polymerization, transition metal catalyst, polymerization method, and the like. It is generally known that an organic metal compound added in a polymerization reaction will act as a chain transfer agent that influences on alkylation of transition metal catalyst, reduction of transition metal catalyst, and molecular weight of a generated polymer. However, if too much organic metal compound is added, the amount of polymethylaluminoxane that activates the transition metal catalyst and suitably stabilizes the activated species is reduced, resulting in low activity when used in polymerization reaction. From these points of view, the ratio of the metal molar quantity of the added organic metal compound, relative to the molar quantity of the aluminum in the polymethylaluminoxane preparation is usually in the range of 10:0.05 to 10:5, and preferably in the range of 10:0.05 to 10:3.

The polymethylaluminoxane preparation according to the present invention contains trimethylaluminum existing therein as an unreacted raw material. In the present invention, the amounts of the polymethylaluminoxane and trimethylaluminum existing in the polymethylaluminoxane preparation are expressed by molar fractions of methyl group originating from the polymethylaluminoxane and the trimethylaluminum (abbreviated as Me(PMAO) and Me(TMAL), respectively).

These molar fractions in the polymethylaluminoxane preparation can be determined by $^1$H-NMR analysis of the polymethylaluminoxane preparation from the area ratios belonging to these components. The transition metal compounds are represented by, for example, the general formula (II):

$$MR^5R^6R^7R^8 \qquad (II)$$

(wherein M represents a transition metal element, and $R^5$, $R^6$, $R^7$, and $R^8$ represent organic groups that form together a cycloalkadienyl backbone, such as an alkyl group, an alkoxy group, an aryloxy group, an alkylsilyl group, an alkylamide group, an alkylimide group, alkylamino group, an alkylimino group, or a halogen atom).

As the "M" in the general formula (II), titanium, zirconium, hafnium, chromium, vanadium, manganese, iron, cobalt, nickel and palladium are recited as concrete examples, with titanium, zirconium chromium, iron, and nickel being preferred.

As a preferred transit metal compound in the general formula (II), a metallocene compound in which one or two ligands having a cycloalkadienyl backbone are coordinated can be exemplified. Examples of the ligand having a cycloalkadienyl backbone include alkyl-substituted cyclopentadienyl groups such as cyclopentadienyl group, methylcyclopentadienyl group, ethylcyclopentadienyl group, butylcyclopentadienyl group, dimethylcyclopentadienyl group and pentamethylcyclopentadienyl group; indenyl group and fluorenyl group, and the cycloalkadienyl group may be bridged with a divalent substituted alkylene group, a substituted silylene group, or the like.

Examples of the ligand other than the ligand having a cycloalkadienyl backbone include hydrocarbon groups having 1 to 20 carbons, alkoxy groups, aryloxy groups, alkylsilyl groups, an amino group, an imino group, halogen atoms, or a hydrogen atom. Examples of the hydrocarbon groups having 1 to 20 carbons include alkyl groups, cycloalkyl groups, aryl groups and aralkyl groups. Concrete examples of the alkyl groups include methyl group, ethyl group, propyl group, isopropyl group, and butyl group; concrete examples of the cycloalkyl groups include cyclopentyl group and cyclohexyl group; concrete examples of the aryl groups include phenyl group and tolyl group; and concrete examples of the aralkyl groups include benzyl group. As the alkoxy groups, a methoxy group, an ethoxy group and a butoxy group are exemplified, and as the aryloxy groups, a phenoxy group can be exemplified. These groups may be substituted with, for example, a halogen atom. As the alkylsilyl groups, a trimethylsilyl group and a triethylsilyl group can be exemplified. As the halogen atoms, fluorine, chlorine, bromine, and iodine can be exemplified.

Concrete examples of the transition metal compounds containing a ligand having a cycloalkadienyl backbone when the "M" in the general formula (II) is zirconium will be listed below. Bis(cyclopentadienyl)zirconium monochloride monohydride, bis(cyclopentadienyl)zirconium monobromide monohydride, bis(cyclopentadienyl)methylzirconium hydride, bis(cyclopentadienyl)ethylzirconium hydride, bis(cyclopentadienyl)phenylzirconium hydride, bis(cyclopentadienyl)benzylzirconium hydride, bis(cyclopentadienyl)neopentylzirconium hydride, bis(methylcyclopentadienyl)zirconium monochloride hydride, bis(indenyl)zirconium monochloride hydride, bis(cyclopentadienyl)zirconium dichloride, bis(cyclopentadienyl)zirconium dibromide, bis(cyclopentadienyl)methylzirconium monochloride, bis(cyclopentadienyl)ethylzirconium monochloride, bis(cyclopentadienyl)cyclohexylzirconium monochloride, bis(cyclopentadienyl)phenylzirconium monochloride, bis(cyclopentadienyl)benzylzirconium monochloride, bis(methylcyclopentadienyl)zirconium dichloride, bis (dimethylcyclopentadienyl)zirconium dichloride, bis(1-butylcyclopentadienyl)zirconium dichloride, bis(indenyl)zirconium dichloride, bis(indenyl)zirconium dibromide, bis(cyclopentadienyl)zirconium dimethyl, bis(cyclopentadienyl)zirconium diphenyl, bis(cyclopentadienyl)zirconium dibenzyl, bis(cyclopentadienyl)zirconium monomethoxy monochloride, bis(cyclopentadienyl)zirconium monoethoxy monochloride, bis(methylcyclopentadienyl)zirconium monoethoxy monochloride, bis(cyclopentadienyl)zirconium monophenoxy monochloride, and bis(fluorenyl)zirconium dichloride. Concrete examples of the transition metal compounds will be listed below when the "M" in the general formula (II) is zirconium and the transit metal compound contains at least two ligands having a cycloalkadienyl backbone, the at least two ligands being bound via an alkylene group such as ethylene or propylene, via a substituted alkylene group such as isopropylidene or diphenylmethylene, via a silylene group or via a substituted silylene group such as dimethyl silylene: ethylene bis(indenyl)dimethylzirconium, ethylene bis(indenyl)diethylzirconium, ethylene bis(indenyl)diphenylzirconium, ethylene bis(indenyl)methyl zirconium monochloride, ethylene bis(indenyl)ethyl zirconium monochloride, ethylene bis(indenyl)methyl zirconium monobromide, ethylene bis(indenyl)zirconium dichloride, and ethylene bis(indenyl)zirconium bromide.

These transition metal compounds may be used singly or in combination of two or more kinds for the purpose of controlling the molecular weight distribution in conducting homogenous polymerization. In the case where a solid catalyst is prepared in advance, one kind of these transition metal compounds may be used, or two or more kinds may be used for the purpose of controlling the molecular weight distribution.

As to the homogenous polymerization using the polymethylaluminoxane preparation of the present invention and polymerization using a supported catalyst using the polymethylaluminoxane preparation of the present invention, suitable performances can be exerted in any polymerization forms, including solution polymerization using a solvent and bulk polymerization and vapor phase polymerization not using a solvent. A desirable performance is realized in both of continuous polymerization and batch polymerization, and hydrogen can be used as a molecular weight controller, if necessary.

Monomers used in polymerization may be any compounds that can be used homopolymerization or copolymerization of olefinic monomers. Concrete examples of such monomers include α-olefins such as ethylene, propylene, 1-buthene, 1-pentene, 1-hexene, 1-decene, 1-hexadecene, 1-octadecene, and 1-eicocene; halogen-substituted olefins such as bisfluoroethylene, trifluoroethylene, tetrafluoroethylene, and hexafluoropropene; and cyclic olefins such as cyclopentene, cyclohexane, and norbornene.

Kinetic viscosity of a polymethylaluminoxane preparation was measured in a temperature-controlled bath at 40° C. under nitrogen atmosphere using a commercially available Ubbelohde viscometer. Specific gravity that is required in converting the kinetic viscosity into a viscosity was measured at 40° C. using a density meter.

EXAMPLES

The present invention will be described in detail by way of working examples, however, the present invention is not limited to these working examples. Any reaction described below was conducted under nitrogen gas atmosphere and solvents were dewatered and degassed before use.

Example 1

(1) Synthesis of Polymethylaluminoxane Preparation

To a separable flask equipped with a stirrer having an inner volume of 2 L, 240.8 g (3.34 mol) of trimethylaluminum (hereinafter, abbreviated as TMAL) and 160.2 g of toluene were introduced. To this solution, 500.1 g of benzoic acid solution in toluene (benzoic acid: 0.49 mol) was slowly added at 26° C. Into this reaction mixture, 89.9 g (0.74 mol) of benzoic acid in powder form was added at 26° C., and then allowed to mature under heating at 50° C. for one hour. At this time, the molar ratio between TMAL and oxygen atoms of benzoic acid was 1.36:1. The reaction mixture was heated at 80° C. for 2 hours, and then heated at 80° C. for additional 6.5 hours, to obtain a polymethylaluminoxane preparation solution in toluene. The resultant solution was transparent liquid not including gels. An Al analysis conducted after collection of the reaction liquid showed a quantitative reaction yield based on the Al atoms. Al concentration of the obtained reaction mixture was 9.3 wt %. Me(TMAL) amount of the resultant polymethylaluminoxane preparation determined by the $^1$H-NMR was 21.4 mol %. Viscosity of the polymethylaluminoxane solution measured by using an Ubbelohde viscometer was $1.71 \times 10^{-3}$ Pa·sec.

The obtained polymethylaluminoxane preparation was subjected to a storage stability test at 25° C. for 90 days, and formation of gels and increase in viscosity were not observed.

(2) Evaluation of Ethylene Polymerization 250 mL of toluene was introduced into a 500-mL four-neck flask equipped with a magnetic stirrer, and heated to 34° C. To this was added a solution of 0.16 g (by Al atom) of polymethylaluminoxane preparation in toluene, followed by dicyclopentadienylzirconium dichloride ($Cp_2ZrCl_2$) so that the molar ratio of Al/Zr was 5000, and then ethylene gas was supplied while elevating the temperature to 40° C. After 10 minutes, supply of ethylene gas was stopped, and the catalyst was inactivated by introduction of methanol. The generated polyethylene was filtered and dried. The polymerization activity was $69 \times 10^6$ g-PE/mol-Zr.atm·hr.

Example 2

(1) Synthesis of Polymethylaluminoxane Preparation

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.30:1. The resultant solution was transparent liquid not including gels. An Al analysis conducted after collection of the reaction liquid showed a quantitative reaction yield based on the Al atoms. Al concentration of the obtained reaction mixture was 9.4 wt %. Me(TMAL) amount of the resultant polymethylaluminoxane preparation determined by the $^1$H-NMR was 18.3 mol %. Solution viscosity of the polymethylaluminoxane preparation measured by using an Ubbelohde viscometer was $1.93 \times 10^{-3}$ Pa·sec.

The obtained polymethylaluminoxane preparation was subjected to a storage stability test at 25° C. for 90 days, and formation of gels and increase in viscosity were not observed.

(2) Evaluation of Ethylene Polymerization

Evaluation of polymerization was conducted in the same manner as described in Example 1. The polymerization activity was 72×10$^6$ g-PE/mol-Zr.atm·hr.

Example 3

(1) Synthesis of Polymethylaluminoxane Preparation

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.40:1. The resultant solution was transparent liquid not including gels. An Al analysis conducted after collection of the reaction liquid showed a quantitative reaction yield based on the Al atoms. Al concentration of the obtained reaction mixture was 9.4 wt %. Me(T-MAL) amount of the resultant polymethylaluminoxane preparation determined by the $^1$H-NMR was 22.6 mol %. Solution viscosity of the polymethylaluminoxane preparation measured by using an Ubbelohde viscometer was 1.60×10$^{-3}$ Pa·sec.

The obtained polymethylaluminoxane preparation was subjected to a storage stability test at 25° C. for 90 days, and formation of gels and increase in viscosity were not observed.

(2) Evaluation of Ethylene Polymerization

Evaluation of polymerization was conducted in the same manner as described in Example 1. The polymerization activity was 70.5×10$^6$ g-PE/mol-Zr.atm·hr.

Example 4

(1) Synthesis of Polymethylaluminoxane Preparation

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.33:1. The resultant solution was transparent liquid not including gels. An Al analysis conducted after collection of the reaction liquid showed a quantitative reaction yield based on the Al atoms. Al concentration of the obtained reaction mixture was 9.4 wt %. Me(T-MAL) amount of the resultant polymethylaluminoxane preparation determined by the $^1$H-NMR was 20.2 mol %. Solution viscosity of the polymethylaluminoxane preparation measured by using an Ubbelohde viscometer was 1.83×10 Pa·sec.

The obtained polymethylaluminoxane preparation was subjected to a storage stability test at 25° C. for 90 days, and formation of gels and increase in viscosity were not observed.

(2) Evaluation of Ethylene Polymerization

Evaluation of polymerization was conducted in the same manner as described in Example 1. The polymerization activity was 70.5×10$^6$ g-PE/mol-Zr.atm·hr.

Example 5

(1) Synthesis of Polymethylaluminoxane Preparation

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.26:1. The resultant solution was transparent liquid not including gels. An Al analysis conducted after collection of the reaction liquid showed a quantitative reaction yield based on the Al atoms. Al concentration of the obtained reaction mixture was 9.3 wt %. Me(T-MAL) amount of the resultant polymethylaluminoxane preparation determined by the $^1$H-NMR was 15.8 mol %. Solution viscosity of the polymethylaluminoxane preparation measured by using an Ubbelohde viscometer was 2.02×10$^{-3}$ Pa·sec.

The obtained polymethylaluminoxane preparation was subjected to a storage stability test at 25° C. Formation of gels and increase in viscosity were not observed by 80 days, however deposition of gels was observed after 80 days.

(2) Evaluation of Ethylene Polymerization

Evaluation of polymerization was conducted in the same manner as described in Example 1. The polymerization activity was 71.0×10$^6$ g-PE/mol-Zr.atm·hr.

Comparative Example 1

(1) Synthesis of Polymethylaluminoxane Preparation

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.23:1. The resultant solution was transparent liquid not including gels. An Al analysis conducted after collection of the reaction liquid showed a quantitative reaction yield based on the Al atoms. Al concentration of the obtained reaction mixture was 9.2 wt %. Me(T-MAL) amount of the resultant polymethylaluminoxane preparation determined by the $^1$H-NMR was 13.0 mol %. Solution viscosity of the polymethylaluminoxane preparation measured by using an Ubbelohde viscometer was 2.36×10$^{-3}$ Pa·sec.

The obtained polymethylaluminoxane preparation was subjected to a storage stability test at 25° C., and deposition of gels was observed after 7 days.

Comparative Example 2

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.20:1. The resultant solution was transparent liquid not including gels. An Al analysis conducted after collection of the reaction liquid showed a quantitative reaction yield based on the Al atoms. Al concentration of the obtained reaction mixture was 9.3 wt %. Me(T-MAL) amount of the resultant polymethylaluminoxane preparation determined by the $^1$H-NMR was 9.2 mol %. Solution viscosity of the polymethylaluminoxane preparation measured by using an Ubbelohde viscometer was 2.76×10$^{-3}$ Pa·sec.

The obtained polymethylaluminoxane preparation was subjected to a storage stability test at 25° C., and deposition of gels was observed after 3 days.

Comparative Example 3

(1) Addition of Trimethylaluminum to Polymethylaluminoxane Preparation

To 102.5 g (Al content: 345.5 mmol, Me(TMAL)=13.0 mol %) of the polymethylaluminoxane preparation prepared in Comparative example 1, 6.1 g (84.3 mmol) of trimethylaluminum was added, and heated at 40° C. for 30 minutes. Me(TMAL) amount of the resultant polymethylaluminoxane preparation determined by the $^1$H-NMR was 19.8 mol %. Solution viscosity of the polymethylaluminoxane preparation measured by using an Ubbelohde viscometer was $2.15 \times 10^{-3}$ Pa·sec.

The obtained polymethylaluminoxane preparation was subjected to a storage stability test at 25° C., and deposition of gels was observed after 14 days.

Comparative Example 4

A polymethylaluminoxane preparation was synthesized in the same manner as described in Example 1 except that the amount of benzoic acid added in powder form in Example 1 was changed so that the molar ratio between TMAL and oxygen atoms of benzoic acid was 1.45:1. The resultant solution was transparent liquid not including gels. An Al analysis conducted after collection of the reaction liquid showed a quantitative reaction yield based on the Al atoms. Al concentration of the obtained reaction mixture was 9.3 wt %. Me(TMAL) amount of the resultant polymethylaluminoxane preparation determined by the $^1$H-NMR was 27.8 mol %. Solution viscosity of the polymethylaluminoxane preparation measured by using an Ubbelohde viscometer was $1.46 \times 10^{-3}$ Pa·sec.

The obtained polymethylaluminoxane preparation was subjected to a storage stability test at 25° C. for 90 days, and formation of gels and increase in viscosity were not observed.

(2) Evaluation of Ethylene Polymerization

Evaluation of polymerization was conducted in the same manner as described in Example 1. The polymerization activity was as low as $51.0 \times 10^6$ g-PE/mol-Zr·atm·hr.

Comparative Example 5

(1) Synthesis of Polymethylaluminoxane Preparation

To a 300-mL round bottomed flask with a stirrer chip therein, 40.85 g (0.34 mol) of acetophenone and 34.8 g of toluene were introduced and inside temperature of the solution was kept at 15° C. To this solution, 57.0 g (TMAL 0.47 mol) of 60 wt % TMAL solution was slowly added from a dropping funnel. Then thermal maturation at 65° C. was conducted for one hour. At this time, the molar ratio between the introduced TMAL and oxygen atoms of acetophenone was 1.38:1. To this reaction mixture, 30.3 g (Al 0.081 mol) of polymethylaluminoxane (Al concentration: 7.21 wt %) was added, and heated at 65° C. for 4 hours, to obtain a solution of polymethylaluminoxane preparation in toluene. The obtained solution was transparent yellow liquid including no gels. An Al analysis conducted after collection of the reaction liquid showed a quantitative reaction yield based on the Al atoms. Al concentration of the obtained reaction mixture was 9.1 wt %. Me(TMAL) amount of the resultant polymethylaluminoxane preparation determined by the $^1$H-NMR was 20.5 mol %. Solution viscosity of the polymethylaluminoxane preparation measured by using an Ubbelohde viscometer was $2.01 \times 10^{-3}$ Pa·sec.

The obtained polymethylaluminoxane preparation was subjected to a storage stability test at 25° C., and deposition of gels was observed after 7 days.

Comparative Example 6

(1) Synthesis of Polymethylaluminoxane Preparation

A polymethylaluminoxane preparation was synthesized in the same manner as Comparative example 1 except that the amount of introduced acetophenone in Comparative example 1 was changed so that the molar ratio between TMAL and oxygen atoms of acetophenone was 1.34:1. The obtained solution was transparent pale yellow liquid including no gels. An Al analysis conducted after collection of the reaction liquid showed a quantitative reaction yield based on the Al atoms. Al concentration of the obtained reaction mixture was 9.3 wt %. Me(TMAL) amount of the resultant polymethylaluminoxane preparation determined by the $^1$H-NMR was 18.2 mol %. Solution viscosity of the polymethylaluminoxane preparation measured by using an Ubbelohde viscometer was $2.23 \times 10^3$ Pa·sec.

The obtained polymethylaluminoxane preparation was subjected to a storage stability test at 25° C., and deposition of gels was observed after 4 days.

Comparative Example 7

(1) Synthesis of Polymethylaluminoxane Preparation

A polymethylaluminoxane preparation was synthesized in the same manner as Comparative example 5 except that the solution concentration was controlled so that the aluminum concentration of the obtained polymethylaluminoxane preparation was 7.5 wt % in Comparative example 5. The obtained solution was transparent pale yellow liquid including no gels. An Al analysis conducted after collection of the reaction liquid showed a quantitative reaction yield based on the Al atoms. Al concentration of the obtained reaction mixture was 7.5 wt %. Me(TMAL) amount of the resultant polymethylaluminoxane preparation determined by the $^1$H-NMR was 23.3 mol %. Solution viscosity of the polymethylaluminoxane preparation measured by using an Ubbelohde viscometer was $1.46 \times 10^{-3}$ Pa·sec.

The obtained polymethylaluminoxane preparation was subjected to a storage stability test at 25° C., and deposition of gels was observed after 8 days.

Comparative Example 8

(3) Evaluation of Storage Stability of Polymethylaluminoxane Preparation

Evaluation was conducted in the same manner as Example 1 except that a commercially available polymethylaluminoxane preparation was used in place of the polymethylaluminoxane preparation used in Example 1. Al concentration of the solution was 8.3 wt %. Me(TMAL) amount of the resultant polymethylaluminoxane preparation determined by the $^1$H-NMR was 47.7 mol %. Solution viscosity of the polymethylaluminoxane preparation measured by using an Ubbelohde viscometer was $0.90 \times 10^{-3}$ Pa·sec.

The obtained polymethylaluminoxane preparation was subjected to a storage stability test at 25° C., and deposition of gels was observed after 10 days.

Comparative Example 9

A polymethylaluminoxane preparation was synthesized in the same manner as Example 1 except that 3 mol % of the polymethylaluminoxane preparation generated in Example 1 was introduced to trimethylaluminum in thermal decomposition of the reaction product from trimethylaluminum and benzoic acid in Example 1. The obtained solution was transparent liquid including no gels. An Al analysis conducted after collection of the reaction liquid showed a quantitative reaction yield based on the Al atoms. Al concentration of the obtained reaction mixture was 9.4 wt %. Me(TMAL) amount of the resultant polymethylaluminoxane preparation determined by the $^1$H-NMR was 22.2 mol %. Solution viscosity of the polymethylaluminoxane preparation measured by using an Ubbelohde viscometer was $1.83 \times 10^{-3}$ Pa·sec.

The obtained polymethylaluminoxane preparation was subjected to a storage stability test at 25° C., and deposition of gels was observed after 30 days.

Comparative Example 10

A polymethylaluminoxane preparation was synthesized in the same manner as Example 1 except that benzophenone was used in place of benzoic acid used as an oxygen source in Example 1, and Al concentration was set to 6.3 wt %. Formation of gels was observed in the obtained reaction solution. According to the Al concentration of the obtained solution, the reaction yield based on the Al atoms was as low as 67%.

Figure 1:
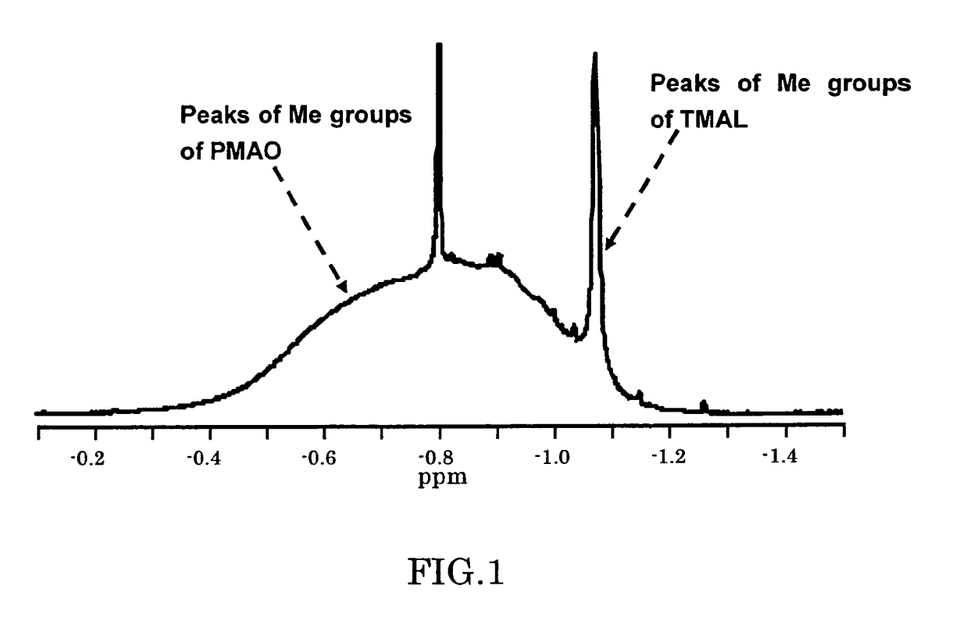
FIG. 1 is a $^1$H-NMR chart of a polymethylaluminoxane preparation according to the present invention.
Figure 2:
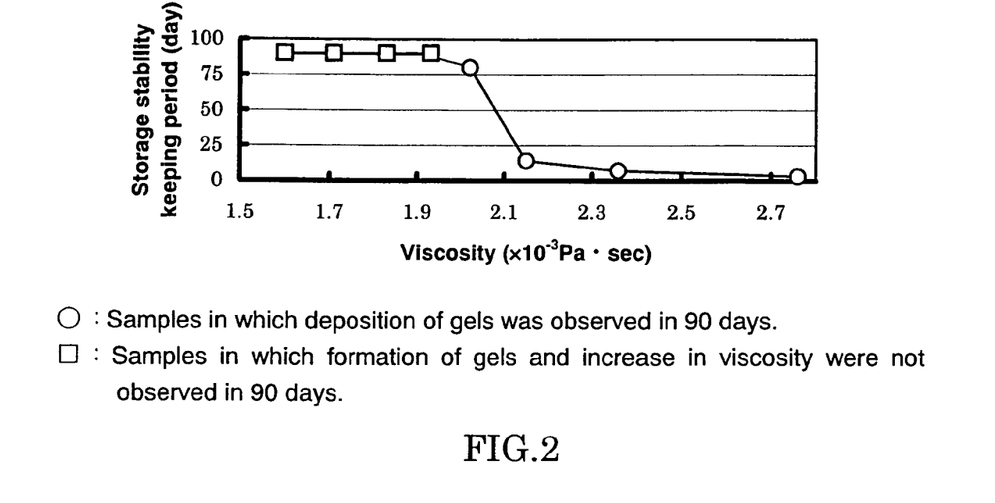
FIG. 2 is a graph showing relationship between viscosity of polymethylaluminoxane preparation and days by which storage stability is kept.

FIG. 2 shows results of storage stability tests of polymethylaluminoxane preparations at 25° C., in which the vertical axis represents viscosity of polymethylaluminoxane solution, and the horizontal axis represent days at which gel deposition was observed. The data plotted in this graph are of Examples 1 to 5 and Comparative examples 1 to 3 for convenience of comparison. This graph shows the specificity of storage stability of polymethylaluminoxane preparation such that there is a critical point when the solution viscosity is considered as a parameter.

The polymethylaluminoxane preparation of the present invention is easy to handle because of low solution viscosity, and keeps the stability for a long term without necessity of refrigeration storage. An olefin polymerization catalyst prepared by combining the polymethylaluminoxane preparation and a transition metal compound exhibits high polymerization activity and stable activity. Therefore, polymethylaluminoxane preparation of the present invention is useful as a promoter for polymerization of polyolefin.

What is claimed is:

1. A polymethylaluminoxane composition generated by thermal decomposition of an alkylaluminum compound having an aluminum-oxygen-carbon bond, the alkylaluminum compound being generated by a reaction between trimethylaluminum and benzoic acid, with toluene as a solvent, wherein:
   (i) a mole fraction of methyl groups originating from trimethylaluminum, relative to the total moles of methyl groups existing in the generated polymethylaluminoxane composition, is not more than 26 mol %;
   (ii) the generated polymethylaluminoxane composition has a viscosity of not more than $2.1 \times 10^{-3}$ Pa·sec at 40° C.,
   (iii) an aluminum concentration of the generated polymethylaluminoxane composition is in a range of from 9.1 wt % to 9.4 wt %, and
   (iv) the generated polymethylaluminoxane composition does not generate gels when stored at 25° C. for 90 days.

2. A method of producing the polymethylaluminoxane composition according to claim 1, the method comprising the steps of:
   causing trimethylaluminum to react with benzoic acid, with toluene as a solvent; and
   thermally decomposing the alkylaluminum compound,
   wherein a ratio between a mole number of trimethylaluminum and a mole number of oxygen in the benzoic acid is in the range of 1.25 to 1.40:1.

3. The method of producing a polymethylaluminoxane composition according to claim 2, wherein
   the thermal decomposition is conducted in the absence of a Lewis acid compound in production of the polymethylaluminoxane composition.

4. A polymerization catalyst for olefins, comprising as catalytic components:
   a transition metal compound represented by the general formula (II), $$MR^5R^6R^7R^8 \tag{II}$$

wherein M represents a transition metal element, and $R^5$, $R^6$, $R^7$, and $R^8$ represent organic groups that form together a cycloalkadienyl backbone, and each is selected from an alkyl group, an alkoxy group, an aryloxy group, an alkylsilyl group, an alkylamide group, an alkylimide group, an alkylamino group, an alkylimino group, or a halogen atom; and
   the polymethylaluminoxane composition according to claim 1.

5. A method of polymerizing olefins in the presence of the polymerization catalyst according to claim 4.

* * * * *